United States Patent [19]

Elkhoury

[11] Patent Number: 5,866,143
[45] Date of Patent: Feb. 2, 1999

[54] TOPICAL APPLICATION OF OPIOID DRUGS SUCH AS MORPHINE FOR RELIEF OF ITCHING AND SKIN DISEASE

[75] Inventor: George F. Elkhoury, Long Beach, Calif.

[73] Assignee: El Khoury and Stein, Ltd., Long Beach, Calif.

[21] Appl. No.: 732,594

[22] Filed: Oct. 15, 1996

Related U.S. Application Data

[63] Continuation of Ser. No. 410,503, Mar. 24, 1995, abandoned.

[51] Int. Cl.$^6$ ..................................................... A61K 7/48
[52] U.S. Cl. ........................... 424/401; 424/43; 514/282; 514/864; 514/944
[58] Field of Search ..................................... 424/401, 282, 424/43; 514/864, 944

[56] References Cited

U.S. PATENT DOCUMENTS

| | | | |
|---|---|---|---|
| 3,275,510 | 9/1966 | Magid et al. | 167/58 |
| 4,416,886 | 11/1983 | Bernstein | 424/260 |
| 4,464,378 | 8/1984 | Hussain | 424/260 |
| 4,493,848 | 1/1985 | Lehann et al. | 424/324 |
| 4,626,539 | 12/1986 | Aungst et al. | 514/282 |
| 4,871,750 | 10/1989 | Roberts | 514/328 |
| 4,897,260 | 1/1990 | Ross et al. | 424/59 |
| 5,069,909 | 12/1991 | Sharma et al. | 424/449 |
| 5,589,480 | 12/1996 | Elkhoury et al. | 514/282 |

FOREIGN PATENT DOCUMENTS 9213540  8/1992  WIPO.

OTHER PUBLICATIONS

Dickenson, "Neurophysiology of Opioid Poorly Responsive Pain" *Cancer Surveys Volume 21: Palliative Medicine: Problem Areas in Pain and Symptom Management*, 1994, pp. 5–16.

Giardina et al., "Central and Peripheral Analgeisc Agents: Chemical Strategies for Limiting Brain Penetration in Kappa–Opioid Agonists Beloning to Different Chemical Classes" Il Farmaco, 50 (6), 1995, pp. 405–418.

Herz, "Role of Immune Processes in Peripheral Opioid Analgesia" *The Brain Immune Axis and Substance Abuse*, 1995, pp. 193–199.

Kinnman et al., "Peripherally Administered Morphine Attenuates Capsaicin–Induced Mechanical Hypersensitivity in Humans" *Anesth Analg*, 1997, pp. 595–599.

Makman, Morphine receptors in immunocytes and neurons *Advances in Neuroimmunology*, vol. 4, 1994, pp. 69–82.

Mather, "Opioids: A Pharmacologists Delight!" *Clinical and Experimental Pharmacology and Physiology* 22, 1995, pp. 833–836.

Needham, "Painless Lumbar Surgery: Morphine Nerve Paste" *Connecticut Medicine*, Mar. 1996, pp. 141–143.

Siddall et al., "Pain Mechanisms and Management: An Update" *Clinical and Experimental Pharmacology and Physiology* 22, 1995, pp. 679–688.

Stein, et al., "No Tolerance to Peripheral Morphine Analgesia in Presence of Opioid Expression in Inflamed Synovia" *J. Clin. Invest.*, vol. 98, No. 3, Aug. 1996, pp. 793–799.

Thompson, et al., "Local Analgesia with Opioid Drugs" *The Annals of Pharmacotherapy*, vol. 29, Feb., 1995, pp. 189–190.

Traynor, et al., "Opioid Receptors and Their Subtypes: Focus on Peripheral Isolated Tissue Preparations" *Neurochem. Int.* vol. 24, No. 5, 1994, pp. 427–432.

An English Language abstract of WO 9213540–A1, dated Feb. 6, 1991.

Stein, "Peripheral and Non–Neuronal Opioid Effects" *Current Opinion in Anesthesiology* (1994), pp.347–351.

Stein, "Peripheral Mechanisms of Opioid Analgesia" *Anesth. Analg.* (1993), pp. 182–191.

Stein et al., "Peripheral Opioid Receptors" *Annals of Medicine* 27 (1995), pp. 219–221.

Stein, "The Control of Pain in Peripheral Tissue by Opioids" *New England Journal of Medicine* vol. 332 No. 25 (1995) pp. 1685–1689.

Tennant et al., "Topical Morphine for Peripheral Pain" in the Letters to the Editor in *The Lancet* vol. 342 (1993) pp. 1047–1048.

Peyman et al., "Effects of morphine on corneal sensitivity and epithelial wound healing: implications for topical ophthalmic analgesia", LSU Eye Center Louisiana State University Medical Center of of Medicine, Accepted for Publication Aug. 26, 1993.

Joris et al., "Opioid Analgesia at Peripheral Sites" *Anesth. Analg.* 66: 1277–1281, International Anesthesia Research Soc., 1987.

Jaffe et al., "Opioid Analgesics and Antagonists" *Goodman and Gilman's The Pharmacological Basis of Therapeutics*, 8th Edition (1990) pp. 485–521.

Reisine et al., "Opioid Analgesics and Antagonists" *Goodman and Gilman's The Pharmacological Basis of Therapeutics*, 9th Edition (1996) pp. 521–555.

Back, et al., "Analgesic Effect of Topical Opioids on Painful Skin Ulcers" in the Letters to the Editor *Journal of Pain Symptom Management*, vol. 10, No. 7, Oct., 1995, p. 493.

*Primary Examiner*—Jyothsan Venkat
*Attorney, Agent, or Firm*—Greenblum & Bernstein P.L.C.

[57] ABSTRACT

The topical application of an opioid analgesic drug to an area of itching and/or skin irritation of a patient, including providing a quantity of an opioid analgesic drug, and mixing the opioid analgesic drug with a non-transdermal carrying agent. Applying the mixture of the opioid analgesic drug and non-transdermal carrying agent to the area of the patient to produce a reduction in itching and/or skin disease.

11 Claims, 1 Drawing Sheet

TOPICAL APPLICATION OF OPIOID DRUGS SUCH AS MORPHINE FOR RELIEF OF ITCHING AND SKIN DISEASE

This application is a continuation of application Ser. No. 08/410,503, filed Mar. 24, 1995, now abandoned.

BACKGROUND OF THE INVENTION

1. Field of the Invention

The present invention is directed to a method for the topical application of opioid analgesic drugs such as morphine. Specifically, the present invention relates to topical application of the opioid drug and specifically a morphine sulphate in a diluted solution to produce a therapeutic effect in an area of itching and/or skin irritations and without a transdermal migration of the opioid drug into the bloodstream.

2. Description of the Prior Art

Itching is an irritating sensation that has some parallels to pain yet is quite different. The mechanisms of pruritus have been closely studied but still are not fully understood. The most likely initiators of the sensation of itching are chemical substances, including endogenous substances like histamine, prostaglandin, epidermal protease, substance P and endopeptides. Lately, some studies have shown that morphine receptors are involved in the mechanism of itching and are studying the use of narcotic antagonists for treatment of itching.

The sensation of itching is conducted slowly along C nerve fibers. Initiation of itching is understood to be the result of certain mediators acting on free nerves ending on the skin within the epidermal junction. Scratching is a unique response to the sensation of itching, thought to be a reflex to remove noxious agents from the skin surface. Scratching brings about a transient sense of relief and may even give pleasure (due to morphine receptors).

Itching may be a localized or generalized phenomenon. Localized itching includes skin disease like psoriasis or scabies or flea bites, which can all produce pruritus. Generalized pruritus can be the result of certain environmental factors, including an excessively dry or humid climate, dry centralized heating, perspiration, overbathing, and harsh soap. The generalized pruritus can also be caused by primary skin disease. Generalized pruritus can also be the result of diseases like internal diseases affecting the endocrine and metabolic-hepatic-renal-hematological system as well as other processes such as cancer. Other causes of itching include injection of drugs like penicillin, drugs which can be harmful to the liver, and illicit drugs.

Treatment:

The optimal therapy for generalized pruritus is treatment of the underlying disease. However, if the etiology has not been determined or if there is no specific treatment, a number of nonspecific palliative therapies exist. Treatment may be topical or systemic. The cooling effect of menthol and the anesthetic effect of phenol or camphor may offer temporary relief for some patients. Low potency topical steroids are good for short term therapy but they are not recommended for chronic use.

When generalized pruritus is treated systemically, it is usually because topical measures have provided no relief. Oral antihistamines are the most commonly used. They act by competitively blocking peripheral histamine receptors, thereby blocking a mode of conduction of itch impulse. The problem with antihistamines is that they produce a sedative effect and rather than directly controlling the itching they could be working by dulling the perception of itching. The problem also is that antihistamines cannot be effective in all cases.

In addition, there have been multiple topical solutions to treat pruritus, including topical capsaicin (Zostrix), which may remove pruritus from patients on hemodialysis. If the pruritus is associated with liver disease, there has been treatment with agents such as rifampin, which are mostly used for tuberculosis, and they have extreme side effects like depression of bone marrow. Of course, there are many other cases where there is no true treatment of pruritus, such as for patients who have diseases that have nonspecific therapies. For example, pruritus or itching associated with AIDS. In those cases many kinds of treatments have been tried without any success, like ultraviolet lights, capsaicin and antihistamines, all without any major relief. Also, the ultraviolet therapy in AIDS patients is bad because ultraviolet affects the T4 lymphocytes and subsequently immunity.

Regardless of its etiology, pruritus which has been present for a long period of time can cause significant frustration for both patients and physician. Thus, it is important for the physician to regularly assess the patient for possible underlying disease and try to find different therapies which will be helpful to the patient without causing any major side effects.

Topical methods:

Combating the urge of scratching is an important part of therapy, so application of a cool, moist washcloth to the area or application of pressure with the palm of the hand near the pruritus area can abate the urge of scratching. Topical preparations may also be used for moisturizing and emollients to fight dryness, but avoiding products with sensitizing potential is vital. Bath oils are most useful in conditions of the skin. A menthol-phenol preparation, for example Noxzema, is helpful as a counterirritant. The major sensitizing benefit of topical corticosteroids has to be weighed against all their potential side effects like corticosteroid addiction and depression of the steroid system in the body.

Oral antihistamines:

Oral medications have been used to treat pruritus, and antihistamines remain the cornerstone of oral therapy. The use of traditional histamine blockers has been limited by the sedative side effects, but all these medications in addition to working partly on pruritus have major side effects like drowsiness. In addition, many of the new drugs, which have been approved by the FDA, produce change in heart rate.

Morphine is the prototype of the class of opioid analgesic drugs which exert their effects by activating opioid receptors within the brain. When morphine is referred to individually in this application, this reference is meant to encompass other opioid drugs and is not meant to be morphine exclusively. Historically, narcotics have been used since the 18th century in the forms of oral or injectable morphine or opium in order to accomplish pain relief. Morphine is considered to be unsurpassed as an analgesic for severe pain.

Unfortunately, morphine and other opioid drugs have a number of severe side effects which hamper their widespread use and acceptance by both physicians and patients. These side effects include: addiction, nausea, inhibition of breathing, somnolence and dysphoria, all of which are mediated by morphine's action within the brain. It is still the current belief that narcotics ingested or injected will cross to the blood stream and from there go to the brain where there are morphine receptors. At that time, the narcotics are believed to attach to these morphine receptors and create a dullness of the pain but with all of the side effects described above. Of course, the worst potential effect is the addiction that can occur if the morphine is used beyond a few days or weeks on a continuous basis.

Reference is made to my earlier invention, made in conjunction with Dr. Christoph Stein, Ser. No. 08/291,614, filed Aug. 17, 1994 wherein the use of a topical application of opioid analgesic to alleviate pain is disclosed. This prior application discusses in detail the use of the topical application of the opioid analgesic and this discussion is incorporated in this application.

SUMMARY OF THE INVENTION

It has now been surprisingly discovered that the topical application of opioid drugs and specifically a morphine sulphate in a diluted solution produces a therapeutic effect in an area of itching and/or skin irritation. The present invention offers a new therapy for itching and/or skin irritations which has no side effects whatsoever and which relieves effectively the itching without side effects.

In the treatment of acute pain postoperative pain or in the treatment of chronic pain (cancer pain), the use of intraspinal narcotics is increasing significantly. With intraspinal narcotics the common complication is itching, mainly in the face and in the hands. To alleviate this itching, the patients are usually treated with antihistamine and cortisone ointment. These medications, such as Benadryl or a topical cortisone, may not provide effective relief for the itching but in addition produce the side effects discussed above.

The second common situation relates to patients who take an oral medication and develop sensitivity to it. For example, when taking antibiotics, to which the patient may be allergic, itching will occur.

Initially, a topical application of opioid drugs was used for five patients who were experiencing intolerable itching. The first four patients were patients who had been treated with long term intraspinal narcotics. These patients originally had significant pain of the upper extremities and lower extremities and they could not find any relief except through injection of intraspinal narcotics. These patients were having good relief from the pain but they were unable to get over the itching. The itching in these four patients was very significant in the face and hands, so the patients discontinued the intraspinal treatment. These patients fell into very severe depression because of the constant pain. Their normal activities were suspended and they were afraid of taking the injection of intraspinal morphine because of the resultant itching which could last for 24 hours. These four patients were asked to try topical morphine gel, which was a combination of 120 cc of K-Y gel with 90 mg of morphine, and to apply 3 cc of this combination on the face and hands and any other area which was itching. After these four patients applied the topical opioid drug of the present invention, they felt relief from the itching within three or four minutes. The patients were able then to enjoy the pain relief that comes with injection of intraspinal morphine, so the patients now are being maintained, and very successfully, on the intraspinal narcotics. The typical treatment is now as follows. After the intraspinal injection, the patients take 3 or 4 cc of the topical opioid drug and rub it on their face, hands and arms and the itching goes away within minutes.

A fifth patient had been taking antibiotics for a medical condition, and every time antibiotics were given, the patient developed a rash on her legs, arms and chest with severe itching. The rash would show as welts on her lower extremities and on her upper extremities and chest and additionally with severe itching in the areas of the welts. The patient scratched all those areas without any relief. The patient was provided with the same cream, 120 cc of K-Y gel with 90 mg of morphine and was asked to rub that cream on her thighs, arms and chest. The patient used a total of 6 cc of this combination, which is less than 3 mg or morphine. The patient felt complete relief within minutes of rubbing the affected areas with the cream and after a period of time the skin irritation was substantially reduced.

None of the five patients reported any side effects, and this could be understandable because the amount of narcotics used is extremely minimal, a total of anywhere from 2 to 5 mg, depending on the area covered. Absorption from the skin is nonexistent, so there are none of the side effects encountered with oral antihistamines like Benadryl. There is no constipation, no nausea, no vomiting and none of the side effects encountered with the use of narcotics for steroids. The relief was uniformly high in those very severe cases which have not been helped with any other treatment. The patients were provided with a total of 120 cc, which would last them anywhere from four to five weeks. The patients were pleased with the results because they had the relief from itching without any side effects.

As to the explanation of why the topical application of narcotics relieves the itching and/or skin irritation, it has been shown that itching is mediated by morphine receptors. All of the laboratory work presently done uses morphine antagonist for relief of itching and we are the only people using morphine agonist.

The above results were accomplished with the use of a small quantity such as less than five milligrams of the opioid drug, such as morphine, diluted to be applied to a relatively large area of skin such as six inches square and without any side effects such as addiction, dullness in the brain, respiratory depression, nausea, vomiting or itching. All of this was accomplished without any significant absorption of the morphine into the blood stream since the morphine was merely applied topically to the skin without any transdermal agent.

In addition to the topical application of the opioid, such as morphine, using a gel, the opioid may be applied using a variety of different topical formulations such as sprays, creams, etc. Depending upon the particular type of itching and/or skin irritations, the topical application will reduce the itching and/or skin irritation. The main advantage is the excellent relief without the typical side effects associated with oral antihistamines or topical cortisone. The potential for the present invention is widespread and the topical application opens up a whole new use of narcotics without the prior associated problems.

DETAILED DESCRIPTION OF THE DRAWINGS

Figure 1:
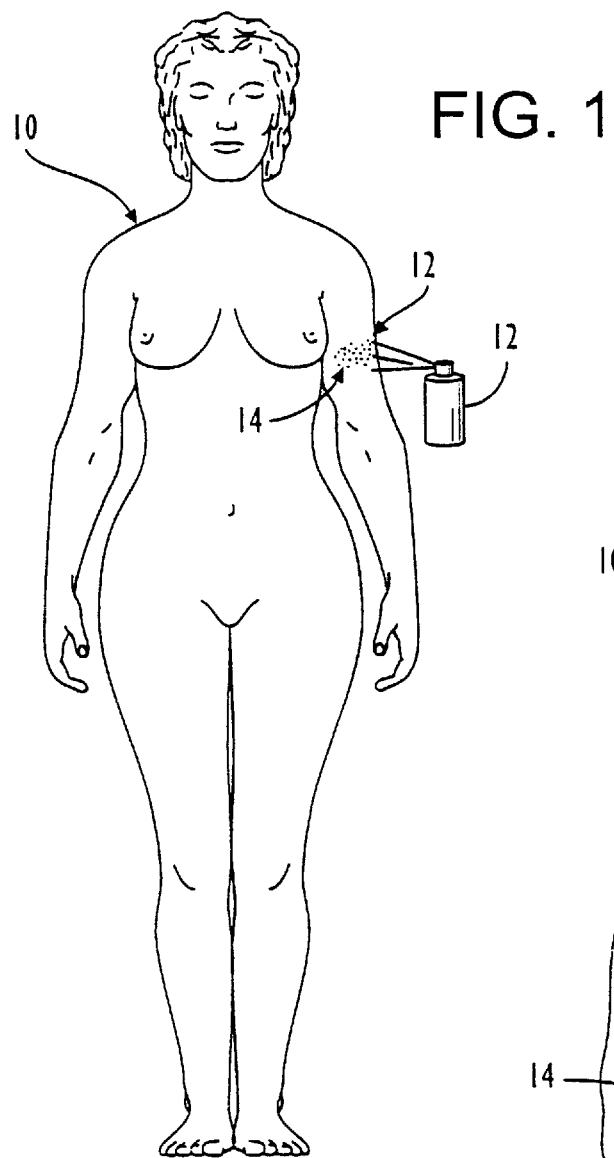
FIG. 1 illustrates a topical application of an opioid drug, such as morphine, using a spray.

FIG. 1 illustrates a method and apparatus of the present invention and specifically shows a patient 10 receiving a topical application of an opioid, such as morphine sulphate using a spray 12. In particular, a small quantity of the morphine sulphate solution is then sprayed onto an area 14 of itching and/or skin irritation on a patient 10 to provide the particular relief described above. As a specific example, 90 milligrams of morphine sulphate may be diluted by 120 cc of saline to form the spray 12. The morphine sulphate is initially provided as a solution of 10 milligrams per cc so that final spray solution is 90 milligrams in a total of 129 cc. Thus, the final concentration of morphine in the spray is 0.69 milligrams per cc. The specific application may result in approximately 2 to 3 milligrams of morphine in solution to cover approximately a 6×6 square inch area.

Figure 2:
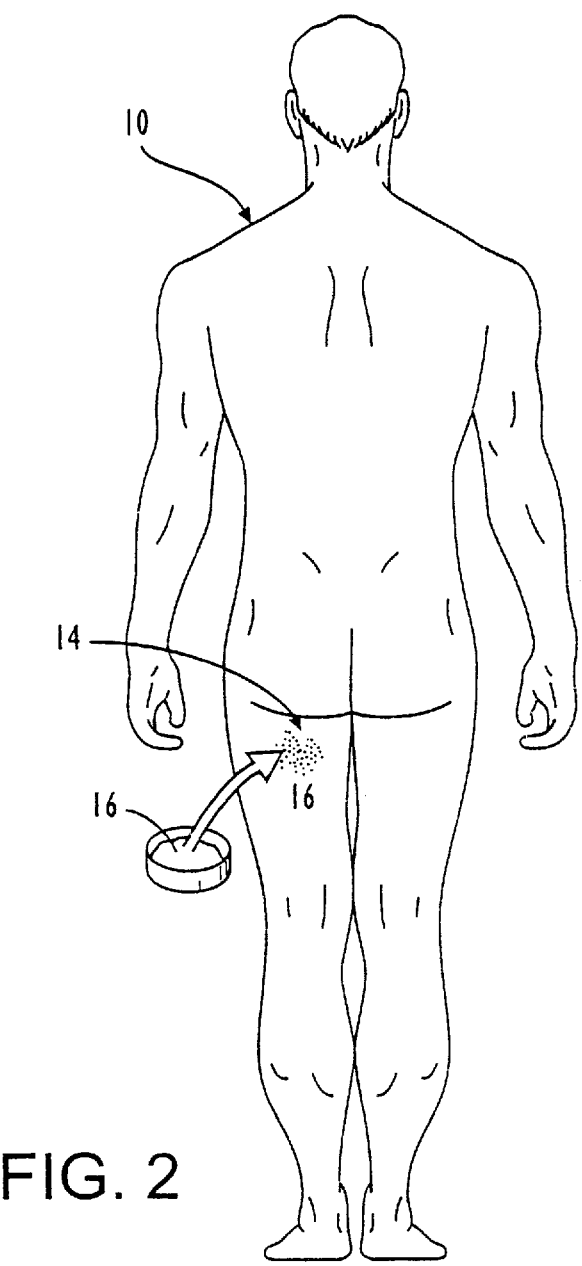
FIG. 2 illustrates a topical application of an opioid drug, such as morphine, using a cream or gel.

FIG. 2 illustrates a patient 10 with an area 14 of itching and/or skin irritation and with an opioid, such as morphine sulphate applied topically in either a gel or a cream 16. As a specific example, 90 milligrams of morphine sulphate may be mixed with 120 cc of a topical gel such as K-Y gel. Again the morphine sulphate is initially provided in solution as 10 mg per cc and with the resultant mixture 16 being 90 mg of morphine sulphate in a total of 129 cc. The resultant gel or cream is applied to the inflamed area 14 so that 2 to 3 mg of morphine sulphate covers an area of approximately 6×6 square inches. Covering a larger area either with a spray or gel will provide for the application of a greater quantity of morphine but over this larger area.

In both methods of application, as shown in FIGS. 1 and 2, the relief is substantial and with continued application on a periodic basis to continue this relief without any of the typical side effects provided by oral antihistamine or topical cortisone. The quantities of the applied opioid described above are illustrative only and it is to be appreciated that lesser and greater quantities may be used. However, any quantity of opioid used in the topical application of the present invention is a small fraction of the typical dosage used in other methods of opioid treatment.

The following is a table of a representative sample of the results achieved with a number of patients listed as follows:

| Patient | Disease | Treatment | Result | Previous Treatment |
|---|---|---|---|---|
| | | PRURITUS PATIENTS | | |
| 1. | Total body itching | Morphine cream cream | Excellent | * Hydrocortisone * Benadryl |
| 2. | Face itching from epidural morphine | Morphine cream | Excellent. Medication used only twice. | * Benadryl |
| 3. | Facial itching from epidural morphine | Morphine cream | Excellent. Medication used only twice. | * Benadryl |
| 4. | Bee sting of hand with swelling and itching | Morphine cream | Excellent. Medication used only once. | * Atarax * Benadryl * Hydrocortisone |
| 5. | Hand itching from psoriasis | Morphine cream | Excellent. Itching disappeared for seven days with single use. | * Hydrocortisone * Benadryl * Atarax |
| 6. | Foot itching from Athlete Foot | Morphine cream | Excellent. Itching improved, but condition did not improve. | * Hydrocortisone * Atarax * Mycotic agent |
| 7. | Total body itching | Morphine cream | Excellent. Total relief of itching within minutes, and welt disappeared within one hour. | * Hydrocortisone * Atarax * Benadryl |
| 8. | Facial itching from Epidural Morphine | Morphine cream | Excellent | * Benadryl |
| 9. | Facial itching from Epidural Morphine | Morphine cream | Excellent | * Benadryl |
| 10. | Acute Herpes Zoster with itching of chest. | Morphine cream | Excellent. Medication used every six hours for three days. | * Benadryl * Hydrocortisone |

| Patient | Disease | Treatment | Result | Previous Treatment |
|---|---|---|---|---|
| | | SKIN DISEASE | | |
| 11 | Acute Herpes Zoster for three weeks | Morphine Cream | Excellent. Relief of pain and improved skin lesions within 3 days. | * Cortisone * Zovirax |
| 12 | Acute Herpes Zoster for 17 days | Morphine Cream | Excellent. Relief of pain and improved skin lesions within 2 days. | * Coritsone * Zovirax |
| 13 | Psoriasis of hands | Morphine Cream | Excellent. Medication used once and skin improved for seven days | * Cortisone |
| 14 | Psoriasis of hand | Morphine Cream | Skin lesions improved with usage. | * Cortisone |

It is to be appreciated that the present invention has been described primarily with reference to the use of morphine in the form of morphine sulphate. Other opioid analgesic drugs and other forms of morphine may be used to interact with the peripheral opioid receptors which are present in peripheral areas of the body and the invention is not to be limited specifically to morphine or morphine sulphate.

Although the invention has been described with reference to a particular embodiment, it is to be appreciated that various adaptations and modifications may be made and the invention is only to be limited by the appended claims.

I claim:

1. A method of treating pruritus in a patient in need of such treatment, comprising topically administering a therapeutically effective amount of an opioid analgesic drug, which amount is ineffective for production of systemic effects, admixed with a pharmaceutically acceptable carrying agent for topical administration.

2. The method of claim 1, wherein the opioid analgesic drug is administered in an amount therapeutically equivalent to up to 5 mg of morphine per 6 square inches of skin.

3. The method of claim 2, wherein the opioid analgesic drug is administered in an amount therapeutically equivalent to 3–5 mg of morphine per 6 square inches of skin.

4. The method of claim 1, wherein the opioid analgesic drug is morphine.

5. The method of claim 1, wherein the opioid analgesic drug is morphine sulfate.

6. The method of claim 1, wherein the carrying agent is a liquid.

7. The method of claim 6, wherein the opioid analgesic drug is administered by spraying onto the skin.

8. The method of claim 1, wherein the carrying agent is a gel.

9. The method of claim 8, wherein the opioid analgesic drug is administered by spreading onto the skin.

10. The method of claim 1, wherein the carrying agent is a cream.

11. The method of claim 10, wherein the opioid analgesic drug is administered by spreading onto the skin.

* * * * *